US008425538B2

(12) United States Patent
Kontos

(10) Patent No.: US 8,425,538 B2
(45) Date of Patent: Apr. 23, 2013

(54) SUTURING DEVICE FOR SEALING A PUNCTURE IN AN ANATOMICAL STRUCTURE

(75) Inventor: Stavros Kontos, Montvale, NJ (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 13/342,885

(22) Filed: Jan. 3, 2012

(65) Prior Publication Data
US 2012/0179174 A1   Jul. 12, 2012

Related U.S. Application Data

(60) Division of application No. 11/594,485, filed on Nov. 7, 2006, now Pat. No. 8,109,944, which is a continuation of application No. 10/418,572, filed on Apr. 17, 2003, now Pat. No. 7,179,266.

(51) Int. Cl.
*A61B 17/04* (2006.01)
(52) U.S. Cl.
USPC .............................. 606/144; 606/139; 606/148
(58) Field of Classification Search .................. 606/139, 606/144, 148, 145, 213, 224, 185, 186, 189
See application file for complete search history.

(56) References Cited

U.S. PATENT DOCUMENTS

| 4,008,303 | A | 2/1977 | Glick et al. |
| 4,518,384 | A | 5/1985 | Tarello et al. |
| 5,368,599 | A | 11/1994 | Hirsch et al. |
| 5,601,572 | A * | 2/1997 | Middleman et al. .......... 606/139 |
| 5,728,114 | A | 3/1998 | Evans et al. |
| 6,010,514 | A | 1/2000 | Burney et al. |
| 6,328,746 | B1 | 12/2001 | Gambale |
| 6,428,549 | B1 | 8/2002 | Kontos |
| 6,436,109 | B1 | 8/2002 | Kontos |
| 6,451,031 | B1 | 9/2002 | Kontos |
| 7,442,198 | B2 | 10/2008 | Gellman et al. |
| 8,109,944 | B2 * | 2/2012 | Kontos .......................... 606/144 |

* cited by examiner

*Primary Examiner* — Tuan V Nguyen
(74) *Attorney, Agent, or Firm* — Holland & Hart

(57) ABSTRACT

A device for automatically providing needles to a sealing apparatus for sealing a puncture in an anatomical structure, the sealing apparatus including a needle insertion lumen and a needle pusher channel having a needle pusher disposed therein. The device may include a housing coupled to the sealing apparatus and a cartridge disposed in the housing. The cartridge has a slot and a plurality of needles disposed, therein. The needle slot is aligned with the needle insertion lumen and the needle pushing channel.

18 Claims, 13 Drawing Sheets

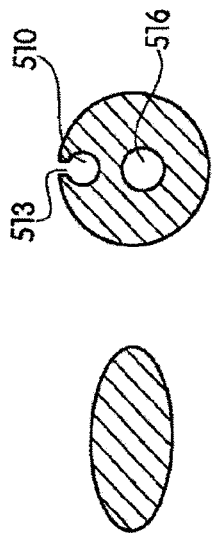
FIG. 3
FIG. 4
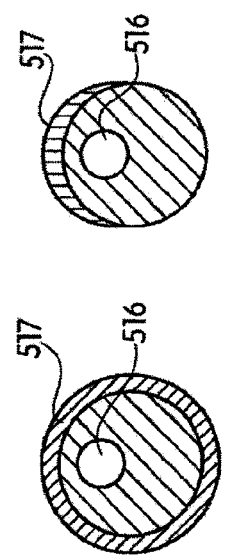
FIG. 5
FIG. 5A
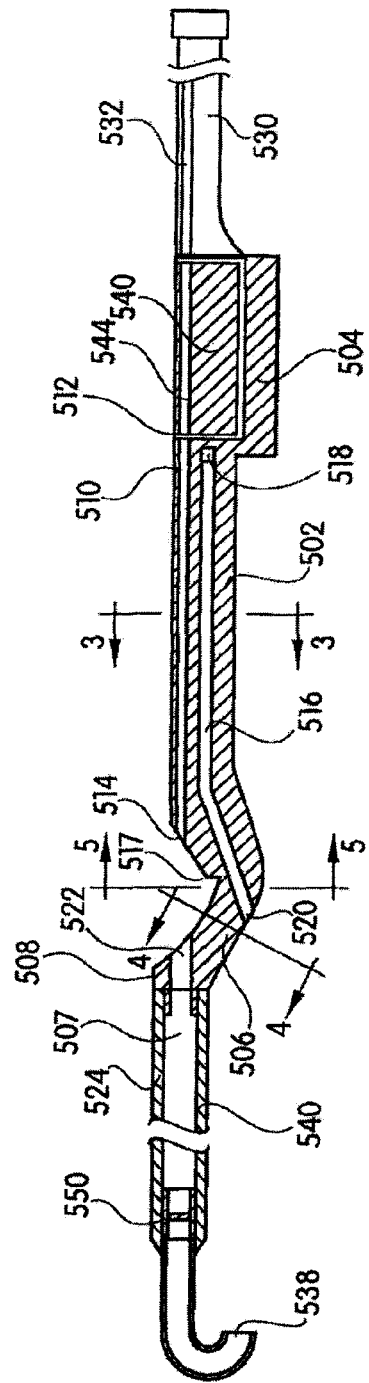
FIG. 2

SUTURING DEVICE FOR SEALING A PUNCTURE IN AN ANATOMICAL STRUCTURE

RELATED APPLICATIONS

This is a divisional of U.S. patent application Ser. No. 11/594,485 filed on 7 Nov. 2006, now issued as U.S. Pat. No. 8,109,944, which is a continuation of U.S. patent application Ser. No. 10/418,572, filed on 17 Apr. 2003, now issued as U.S. Pat. No. 7,179,266, the disclosures of which are incorporated in their entireties by this reference.

FIELD OF THE INVENTION

The present invention relates generally to surgical instruments, and more specifically to a system and method for automatically providing needles to a device for the suturing of punctures in an anatomical structure, e.g., a blood vessel.

BACKGROUND INFORMATION

Many surgical procedures require the insertion of catheters and/or surgical devices into blood vessels and other anatomical structures. For example, in the treatment of vascular disease, it is often necessary to insert an instrument such as a catheter into a blood vessel to perform a treatment procedure. Such treatment procedures often involve piercing a wall of the blood vessel, inserting an introducer sheath into the blood vessel via the opening, and maneuvering the catheter through the introducer sheath to a target location within the blood vessel. Of course, once such a procedure is completed, the opening in the wall of the blood vessel must be sealed to prevent bleeding and to facilitate healing of the wound. The sealing of the puncture has commonly been accomplished by the application of direct pressure over the puncture site by a physician or other trained medical professional. However, this technique is time consuming and may lead to complications such as thrombosis, which may be dangerous to the patient.

Other sealing techniques include the application of a sealing member or plug of material (most often biogenic sealing material) over the opening in the blood vessel to seal the wound. However, proper placement of sealing members and plugs is difficult to achieve and materials left inside the body may pose serious health risks to the patient if, for example, the material enters the blood stream.

Another sealing technique that may be employed to prevent bleeding while facilitating healing of the wound is the use of a suture. Applicant's U.S. Pat. No. 6,451,031 (hereinafter "the '031 patent"), entitled "Blood Vessels Suturing Device With Single Guide-Wire/Needle Receiving Lumen", which issued on Sep. 17, 2002, describes a device that employs a suture to seal a puncture in an anatomical structure. The '031 patent describes a device for sealing a tissue puncture including proximal and distal portions offset by a connecting member so that a needle may exit a lumen in the proximal portion through a needle insertion opening across a tissue receiving gap and enter through a needle receiving opening into a lumen in the distal portion. The distal lumen also has an opening for a guide wire. A method for sealing a tissue puncture by inserting a device such as that described above into the puncture via a guide wire, which is removed, so that the tissue is within the tissue receiving gap, and inserting a first suture needle distally from the proximal lumen, through the tissue, and into the distal lumen. The device is then rotated and a second suture needle similarly penetrates the tissue at a second location, and the device is withdrawn and the suture is tightened. The '031 patent is incorporated by reference herein as fully as if set forth in its entirety.

Applicant's U.S. Pat. No. 6,436,109 (hereinafter "the '109 patent"), entitled "Device and Method for Suturing Blood Vessels and the Like", which issued on Aug. 20, 2002, and Applicant's U.S. Pat. No. 6,428,549 (hereinafter "the '549 patent"), entitled "Device and Method for Suturing Blood Vessels and the Like", which issued on Aug. 6, 2002, describe devices for sealing a puncture in an anatomical structure comprising a proximal portion having a first needle lumen extending therethrough to a first needle opening. The '109 and '549 patents also states that the device includes a distal portion including a second needle opening facing the first needle opening across a tissue receiving gap and opening into a second needle lumen and a connecting portion coupled between the proximal and distal portions and offset from the proximal and distal portions to create the tissue receiving gap. According to the '109 and '549 patents, when the connecting portion is received within a puncture in an anatomical structure, a portion of the anatomical structure received within the tissue receiving gap is located on one side of a plane including a central axis of the puncture. The '109 and '549 patents are incorporated by reference herein as fully as if set forth in their entirety.

These patents have in common the use of several needles in connection with the process of sealing the puncture in an anatomical structure. However, each of the devices described in these patents requires that the needles be handled by a surgeon. The handling of needles by a surgeon during a surgical procedure may be problematic. The needles are thin and difficult to handle, particularly with regards to loading the needles into the small lumens through which the needles are maneuvered during the surgical procedure. Furthermore, blood or other anatomical substances may be present in the vicinity of the procedure, making it still more difficult for the surgeon to handle the needles.

SUMMARY OF THE INVENTION

The present invention is directed to a device for automatically providing needles to a sealing apparatus for sealing a puncture in an anatomical structure, the sealing apparatus including a needle insertion lumen and a needle pusher channel having a needle pusher disposed therein. In accordance with one embodiment of the present invention, the device includes a housing coupled to the sealing apparatus and a cartridge disposed in the housing. The cartridge has at least a first and a second needle slot extending from a distal end of the cartridge to a proximal end of the cartridge. The first and second needle slots have first and second needles disposed, e.g., pre-loaded, therein, respectively. The cartridge is moveable relative to the housing between a first position in which the first needle slot is aligned with the needle insertion lumen and the needle pushing channel, and a second position in which the second needle slot is aligned with the needle insertion lumen and the needle pushing channel.

According to one embodiment of the present invention, the device also includes a biasing element configured to bias the cartridge relative to the housing between the first position and the second position. The biasing element may be a spring element, such as a leaf spring. Furthermore, the needle cartridge may include more than two needle slots, each needle slot having a needle disposed therein.

In accordance with another embodiment, the present invention includes a method for sealing a puncture in an anatomical structure. The method includes the step of disposing at least a first and a second needle in corresponding first and second needle slots of the needle cartridge, the needle cartridge being arranged in a housing of a suture device. The suture device is positioned in the puncture in a first suture position, e.g., so as to receive a blood vessel wall on a first side of a puncture within a tissue receiving gap formed by the suture device. The needle cartridge is positioned in a first position relative to the housing, and the first needle is actuated, such as by a needle pusher pushing the first needle through the suture device and through the blood vessel wall. The suture device is then positioned in the puncture in a second suture position, e.g., so as to receive the blood vessel wall on a second or opposite side of the puncture within the tissue receiving gap formed by the suture device. The needle cartridge is then positioned in a second position relative to the housing, such as by biasing the needle cartridge relative to the housing. The second needle is then actuated, such as by the needle pusher pushing the second needle through the suture device and through the second location of the blood vessel wall.

BRIEF DESCRIPTION OF THE DRAWINGS

FIG. 2 shows a cross-sectional side view of the device of FIG. 1;

FIG. 3 shows a cross-sectional view of the device of FIG. 2 taken along line 3-3 of FIG. 2;

FIG. 4 shows a cross-sectional view of the device of FIG. 2 taken along line 4-4 of FIG. 2;

FIG. 5 shows a cross-sectional view of the device of FIG. 2 taken along line 5-5 of FIG. 2;

FIG. 5A shows an alternative cross-sectional view of the device of FIG. 2 taken along 5-5 of FIG. 2;

DETAILED DESCRIPTION

Figure 1:
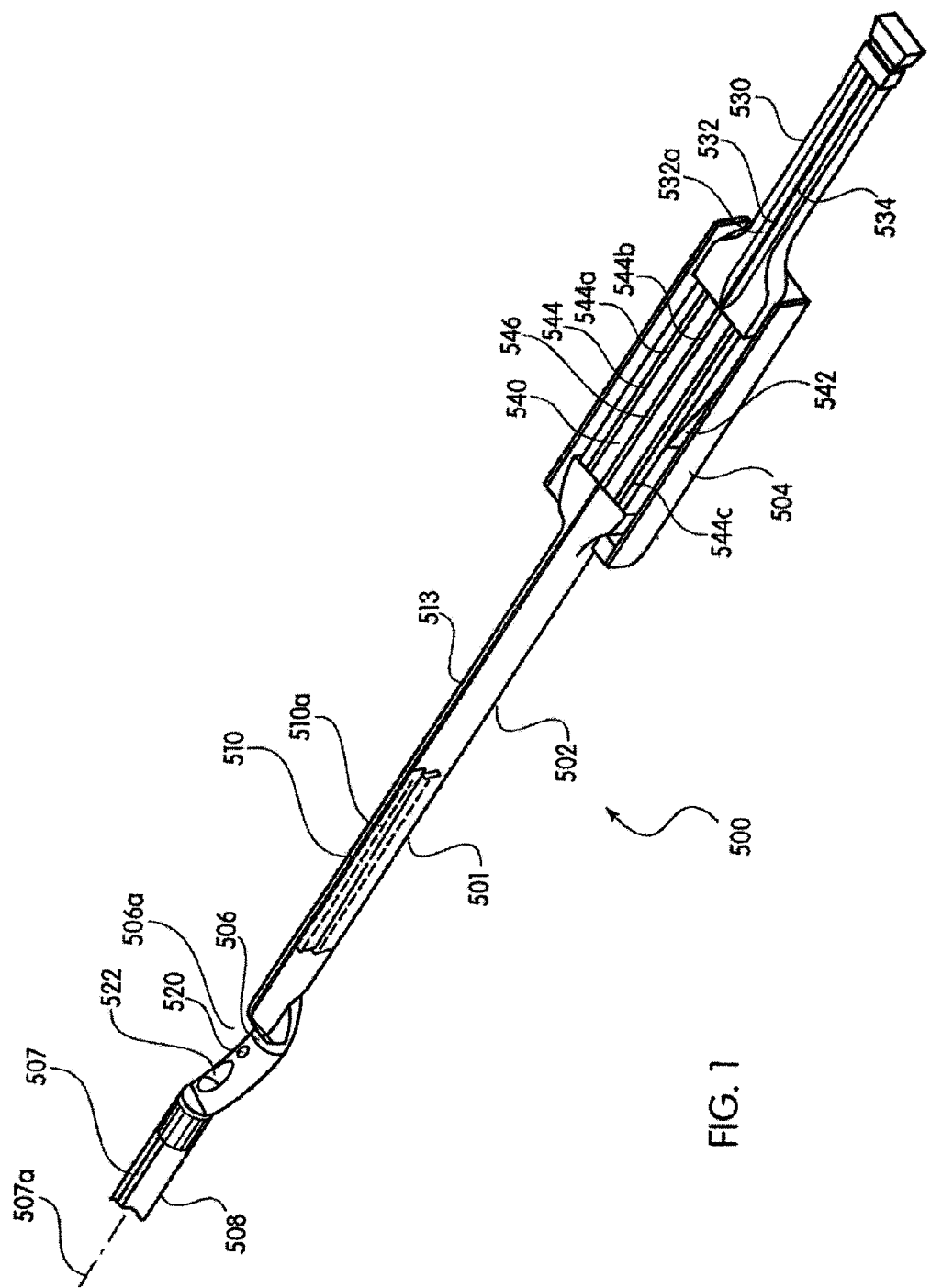
FIG. 1 shows a perspective view of one embodiment of a suturing device according to the present invention.

FIG. 1 shows a suture device 500 according to one embodiment of the present invention. The suture device 500 includes a tube 501 having a substantially circular cross-section. The suture device 500 includes a distal part 508 that defines a distal lumen 507 having a central axis 507a, a proximal part 502 that defines a needle insertion lumen 510 having a central axis 510a, and a housing 504 attached to a proximal end of the proximal part 502. A suture removal slot 513 extends along the surface of the proximal part 502 and communicates with the needle insertion lumen 510 so as to open an interior of the needle insertion lumen 510 to the outside of the device 500 along an entire length of the needle insertion lumen 510. As shown in FIG. 3, a width of the suture removal slot 513 is less than a diameter of a needle inserted through the needle insertion lumen 510 so that a needle received in the needle insertion lumen 510 can not escape from the needle insertion lumen 510 via the suture removal slot 513.

Referring back to FIG. 1, a central part 506 is coupled to a distal end of the proximal part 502 and to a proximal end of the distal part 508 so as to attach the proximal part 502 and the distal part 508 to each other. The central part 506 curves away from the proximal part 502 in the shape of an arc, and returns to connect to the distal part 508. A distal end of the proximal part 502 faces a proximal end of the distal part 508 across a tissue receiving gap 506a formed by the curvature of the central part 506. Advantageously, the proximal part 502, the central part 506 and the distal part 508 are configured such that the central axis 507a of the distal lumen of the distal part 508 is aligned with the central axis 510a of the needle insertion lumen 510 of the proximal part 502.

A cross-sectional area of the central part 506 may be substantially equal to that of the distal part 508 and the cross-sectional areas of both the central part 506 and the distal part 508 may remain substantially constant along their entire lengths while a cross-sectional area of the proximal part 502 may preferably be equal or slightly greater than that of the distal part 508 and the central part 506. More specifically, in a preferred embodiment, a maximum outer diameter of the distal part 508 is no larger than a maximum outer diameter of the central part 506. In this way, the opening in the blood vessel is not further stretched by the introduction of the distal part therethrough. FIG. 4 illustrates one embodiment of the invention wherein the arcuate portion of central part 506 has an oval cross section. The oval cross section allows the arcuate structure to be thinner in a first direction with respect to the tissue receiving gap 506a so that the tissue receiving gap 506a can be deeper, thereby enabling the needle to penetrate the blood vessel wall at a farther distance from the edge of the puncture to be sealed, as described in additional detail below. By enabling the needle to penetrate the blood vessel wall at a farther distance from the edge of the puncture to be sealed, a more stable and secure suture may be possible. The central part 506 of the suture device 500 may also include a ridge. FIG. 5 illustrates one embodiment, wherein the rigid arcuate member of central part 506 includes a raised ridge 517 serving as a catch, or stop, to assist in accurate placement of the suture device 500. Preferably, the raised ridge 517 is located on a proximal side of the central part 506 so that when the suture device 500 is inserted into a puncture in a blood vessel the edge of the puncture will catch on the ridge 517 when the suture device 500 has reached the appropriate depth, as described in additional detail below. The ridge 517 may be formed inside the concave portion of the central part 506, as depicted in FIG. 5 or may be formed around the entire circumference as shown in FIG. 5A.

Referring back to FIG. 1, and as previously mentioned, the suture device 500 includes a housing 504. A distal end of the housing 504 is attached to a proximal end of the proximal part 502. In addition, a proximal end of the housing 504 is attached to needle pusher housing 530. The needle pusher housing 530 defines a needle pusher channel 532 in which is disposed a needle pusher 534. The needle pusher 534 is axially slidable within the needle pusher channel 532 along a central axis 532a of the needle pusher channel 532. Advantageously, the proximal part 502, the housing 504 and the needle pusher housing 530 are configured such that the central axis 510a of the needle insertion lumen 510 of the proximal part 502 is aligned with the central axis 532a of the needle pusher channel 532 of the needle pusher channel 532.

The housing 504 houses a needle cartridge 540. The needle cartridge 540 includes a plurality of needle slots 544 in which needles 546 are disposed. The needle slots 544 are preferably arranged parallel to each other and extend from a distal end to a proximal end of the needle cartridge 540. In the embodiment shown in FIG. 1, the needle cartridge 540 has three needle slots 544. The needle cartridge 540 is moveable within the housing 504 between at least a first and a second position. In one embodiment, the housing 504 includes a spring element 542, such as a leaf spring or other suitable spring element, that contacts the needle cartridge 540 so as to move the needle cartridge 540 within the housing 504 between at least the first and second positions. In the embodiment shown in FIG. 1, the spring element 542 contacts the needle cartridge 540 so as to move the needle cartridge 540 within the housing 504 between three positions. In a first position, the needle cartridge 540 is positioned such that a first needle slot 544a is aligned with the central axis 532a of the needle pusher channel 532 and with the central axis 510a of the needle insertion lumen 510 of the proximal part 502. In a second position, as shown in FIG. 1, the needle cartridge 540 is positioned such that a second needle slot 544b is aligned with the central axis 532a of the needle pusher channel 532 and with the central axis 510a of the needle insertion lumen 510 of the proximal part 502. In a third position, the needle cartridge 540 is positioned such that a third needle slot 544c is aligned with the central axis 532a of the needle pusher channel 532 and with the central axis 510a of the needle insertion lumen 510 of the proximal part 502.

FIG. 2 is a cross-sectional view of the suture device 500 illustrated in FIG. 1. In the embodiment shown, the needle insertion lumen 510 extends through the proximal part 502 from a needle insertion opening 512 formed in a proximal end of the proximal part 502 to an opening 514 formed at a distal end of the proximal part 502. In addition, a position indication lumen 516 extends from an opening 518 formed in the housing 504 through a portion of the central part 506 to an opening 520 formed in the central part 506. A needle receiving opening 522 formed in the proximal end of the distal part 508 extends into the distal lumen 507 which extends axially through the distal part 508. The distal lumen 507 extends for a length at least twice the length of the needles 546 which are to be used with the suture device 500.

The suture device 500 is preferably substantially rigid from the proximal end of the needle pusher housing 530 to the needle entry opening 522 at the proximal end of the distal part 508, and, according to one embodiment, is integrally formed. In addition, the distal part 508 of the suture device 500 is preferably flexible, e.g., with a flexible tube connected to a distal end of the central part 506 and extending distally therefrom. This rigid structure ensures that the central axes 532a, 510a and 507a of the needle pusher channel 532, the needle insertion lumen 510 and the distal lumen 507, respectively, remain properly aligned with one another during operation of the suture device 500. The distal lumen 507 extends through the distal part 508 from the needle receiving opening 522 to a guide wire opening 538.

The distal part 508 is primarily made as a flexible tube 524 which may, e.g., preferably be constructed of a thermoplastic such as polyurethane, polyethylene, or the like. The flexibility of the distal part 508 allows the distal part 508 to bend and follow the direction of the blood vessel without straining the blood vessel. In one embodiment, as shown in FIG. 2, a distal end of the distal part 508 is biased so that, when in an unstressed state, it is "J" shaped. Specifically, the distal portion of the distal part 508 is curved so that the guide wire opening 538 faces proximally. This facilitates insertion of the device 500 so that it contacts an inner wall of the blood vessel without damaging it. Specifically, the flexibility and "J" shape of the flexible tube 524 allows it to deflect away from the blood vessel's lining without penetrating or damaging the lining. Of course, when received on the guide wire, the "J" shape of the flexible tube 524 will be less pronounced. However, the bias will maintain a slight curvature of the flexible tube 524 deflecting the impact of the device 500 from the inside lining of the blood vessel. The flexible tube 524 may also, however, be formed as a straight member or any other shape, as dictated by the shape of the anatomical structure and surrounding tissues.

In one embodiment, the distal lumen 507 contains a valve 550 to prevent blood from flowing through the distal lumen 507 during insertion of the device into the puncture. Without a valve to prevent the flow of blood through the distal lumen 507 blood may escape through the distal lumen 507 while the device is being inserted into a blood vessel. Such excess blood could cause an undesirable condition such as hematoma. In the preferred embodiment, the valve 550 should be positioned in a distal end of the distal lumen 507 so as to not inhibit the ability of the distal lumen 507 to receive suturing needles 546.

Figure 7:
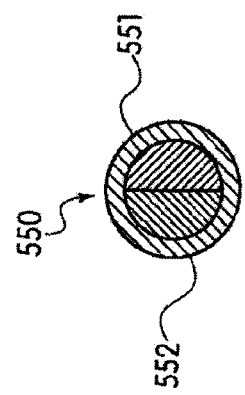
FIG. 7 shows an end view, taken along line 7-7 of FIG. 6, of a preferred embodiment of a valve for placement in a distal lumen.
Figure 6:
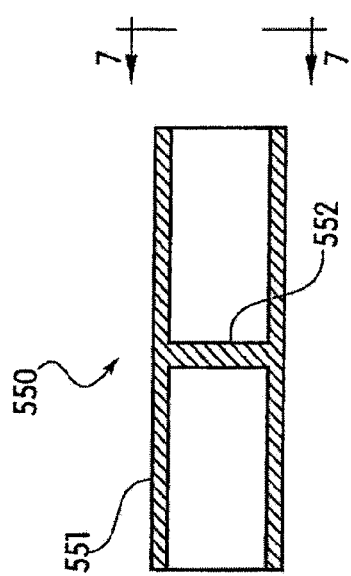
FIG. 6 shows a side cross-section view of a preferred embodiment of a valve for placement in a distal lumen.

FIGS. 6 and 7 illustrate side cross-sectional and front views, respectively, of the valve 550 according to one embodiment of the present invention. In the embodiment shown, the valve 550 includes a cylindrical tube 551, which may be made, for example, of a flexible material such as polyurethane or silicone. The tube 551 is placed coaxially in the distal lumen 507. The valve 550 also includes a slitted diaphragm 552, which may also be constructed of flexible material, situated in the interior cross section of the cylindrical tube 551. The rigidity of the material comprising the slitted diaphragm 522 will substantially prevent blood from flowing through the slitted diaphragm. However, the slitted diaphragm 522 is flexible enough to allow a guide wire to be pushed therethrough during insertion of the device 500 into a blood vessel.

Figure 13A:
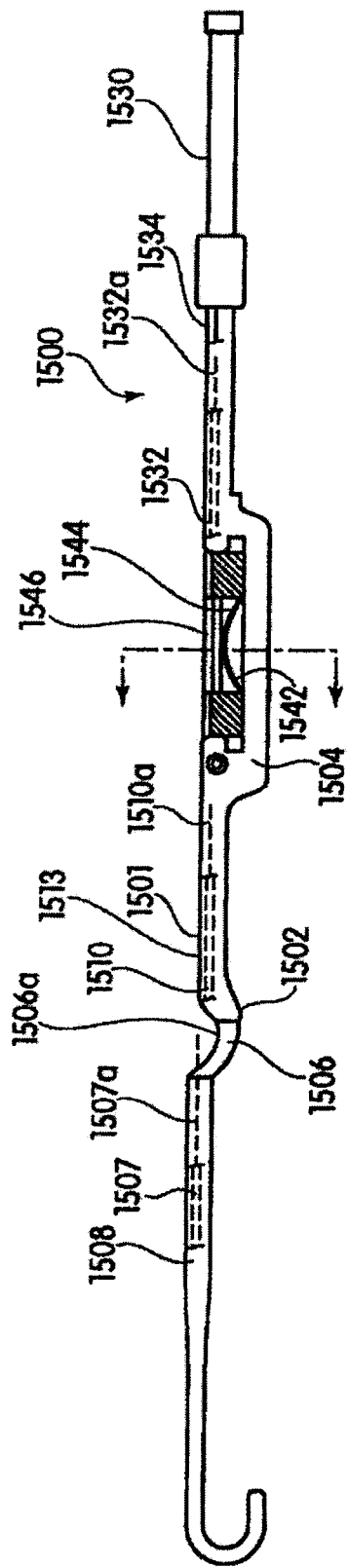
FIGS. 13a and 13b show a suture device 1500 according to another embodiment of the present invention.
Figure 13B:
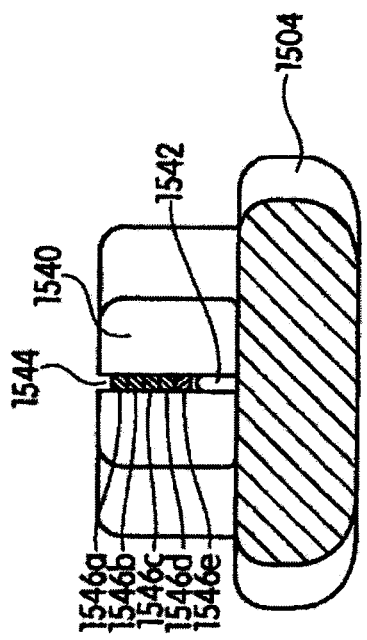

FIGS. 13a and 13b show a suture device 1500 according to another embodiment of the present invention. The suture device 1500 includes a tube 1501 having a substantially circular cross-section. The suture device 1500 includes a distal part 1508 that defines a distal lumen 1507 having a central axis 1507a, a proximal part 1502 that defines a needle insertion lumen 1510 having a central axis 1510a, and a housing 1504 attached to a proximal end of the proximal part 1502. A suture removal slot 1513 extends along the surface of the proximal part 1502 and communicates with the needle insertion lumen 1510 so as to open an interior of the needle insertion lumen 1510 to the outside of the device 1500 along an entire length of the needle insertion lumen 1510. As described more fully above in connection with the suture removal slot 513 of the suture device 500 shown in FIG. 1, a width of the suture removal slot 1513 is less than a diameter of a needle inserted through the needle insertion lumen 1510 so that a needle received in the needle insertion lumen 1510 can not escape from the needle insertion lumen 1510 via the suture removal slot 1513.

A central part 1506 is coupled to a distal end of the proximal part 1502 and to a proximal end of the distal part 1508 so as to attach the proximal part 1502 and the distal part 1508 to each other. The central part 1506 curves away from the proximal part 502 in the shape of an arc, and returns to connect to the distal part 1508. A distal end of the proximal part 1502 faces a proximal end of the distal part 1508 across a tissue receiving gap 1506a formed by the curvature of the central part 1506. Advantageously, the proximal part 1502, the central part 1506 and the distal part 1508 are configured such that the central axis 1507a of the distal lumen of the distal part 1508 is aligned with the central axis 1510a of the needle insertion lumen 1510 of the proximal part 1502.

The suture device 1500 includes a housing 1504. A distal end of the housing 1504 is attached to a proximal end of the proximal part 1502. In addition, a proximal end of the housing 1504 is attached to needle pusher housing 1530. The needle pusher housing 1530 defines a needle pusher channel 1532 in which is disposed a needle pusher 1534. The needle pusher 1534 is axially slidable within the needle pusher channel 1532 along a central axis 1532a of the needle pusher channel 1532. Advantageously, the proximal part 1502, the housing 1504 and the needle pusher housing 1530 are configured such that the central axis 1510a of the needle insertion lumen 1510 of the proximal part 1502 is aligned with the central axis 1532a of the needle pusher channel 1532 of the needle pusher channel 1532.

The housing 1504 houses a needle cartridge 1540. The needle cartridge 1540 includes a needle slot 1544 in which needles 1546 are disposed. FIG. 13b illustrates a cross-sectional view of the needle cartridge 1540. The needle slot 1544 extends from a distal end to a proximal end of the needle cartridge 1540. In the embodiment shown in FIGS. 13a and 13b, the needle slot 1544 is arranged vertically. However, according to various other embodiments of the present invention, the needle slot 1544 is not arranged vertically. Furthermore, the needle slot 1544 is shown having fives needles, e.g., the needles 1546a to 1546e, disposed therewithin. However, the present invention contemplates that the needle slot 1544 may be configured to include any number of needles 1546. The needles 1546 are moveable within the needle slot 1544 such that the needles are successively positioned in alignment with the needle pusher channel 1532 and the needle insertion lumen 1510. In one embodiment, the housing 1504 includes a spring element 1542, such as a leaf spring or other suitable spring element, that contacts at least one of the needles 1546 so as to move the needles 1546 within the needle slot 1544. For instance, as shown in FIG. 13(b), in one embodiment of the present invention, the spring element 1542 contacts lower needle 1546e so as to bias all of the needles 1546 within the needle slot 1544 upwards, such that the uppermost needle 1546a is aligned with the needle pusher channel 1532 and the needle insertion lumen 1510. Once the uppermost needle 1546a is employed, e.g., pushed out of the needle slot 1544 during operation of the device, the spring element 1542 biases the remaining needles 1546 upwards so that the second uppermost needle, e.g., needle 1546b, is automatically aligned with the needle pusher channel 1532 and the needle insertion lumen 1510.

Figure 8:
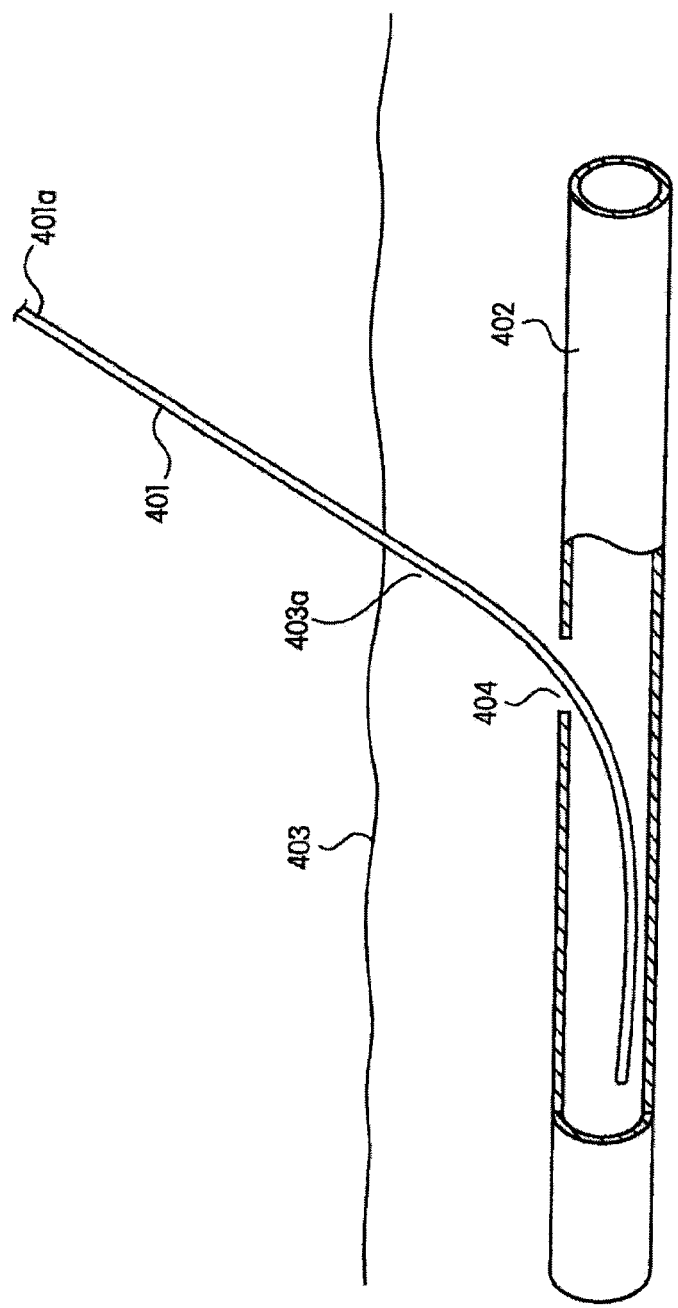
FIG. 8 shows a partial cross-section side view of a guide wire in an initial position within a blood vessel.

FIGS. 8 to 12 illustrate the operation of the suture device 500, according to the embodiment of the present invention shown in FIGS. 1 and 2. In operation, as shown in FIG. 8, when an invasive procedure has been performed on a patient and a catheter previously inserted into a blood vessel 402 (or other structure within the body) has been withdrawn, a guide wire 401 may be left in place extending through the skin 403, through the tissue tract 403a, through the puncture 404 and into the blood vessel. A suture device, such as the suture device 500, may then be used to seal the puncture 404.

Figure 9:
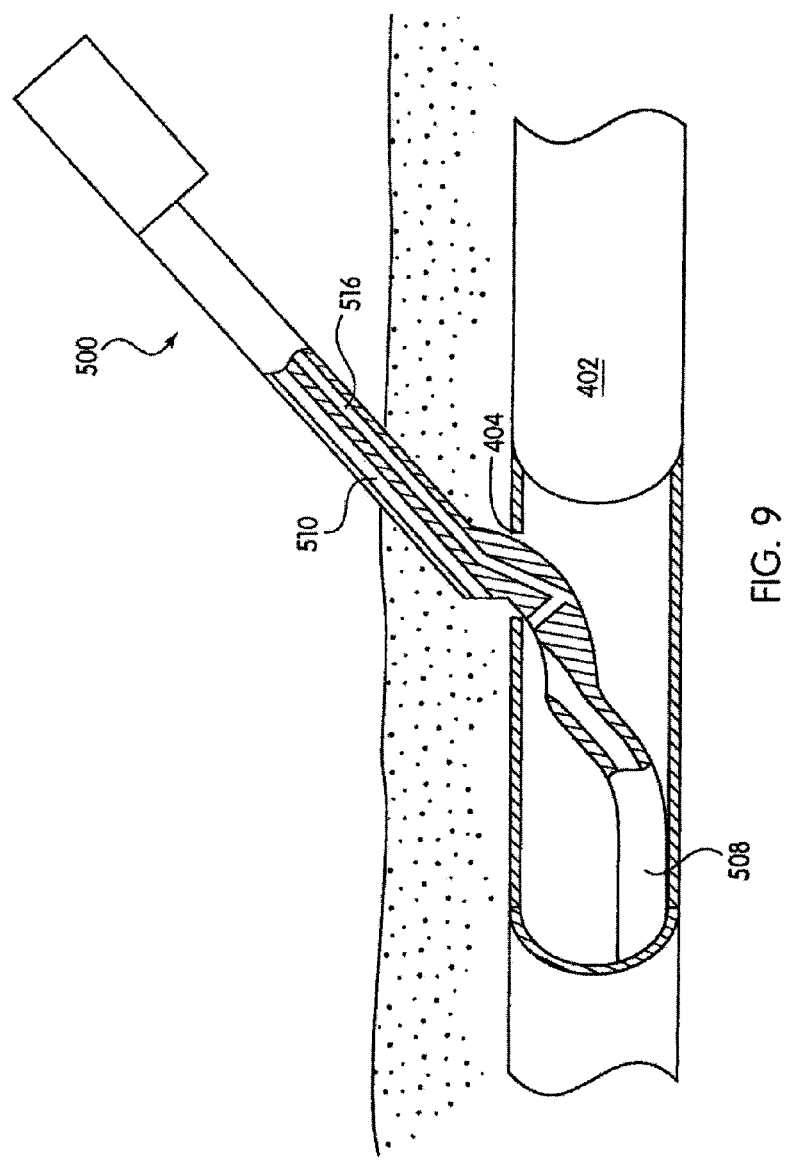
FIG. 9 shows a partial cross-section side view of the device of FIG. 1 inserted in to a blood vessel via a guide wire.

In one embodiment, a proximal end 401a of the guide wire 401 is inserted through the distal lumen 507 so that the suture device 500 may be inserted into the puncture 404 and moved along the guide wire 401 through the puncture 404. FIG. 9 illustrates the distal end 508 of the suture device 500 inserted into the puncture 404. During the insertion and placement of the suture device 500 in the puncture 404, the valve 550 in the distal lumen 507 substantially prevents blood from flowing from the blood vessel 402, through the distal lumen 507, and into the patient's wound. The guide wire 401 may be withdrawn as the central part 506 enters through the skin 403.

The device 500 is determined to be in the desired position by observation of the position indication lumen 516 and the needle insertion lumen 510. Specifically, when the suture device 500 is inserted the correct distance in the blood vessel 402, blood will be observed in the position indication lumen 516. However, if blood is also observed in the needle insertion lumen 510, it is determined that the device 500 has been inserted too far into the blood vessel 402. When properly positioned within the blood vessel 402, the device 500 is rotatable between various desired orientations.

Figure 10:
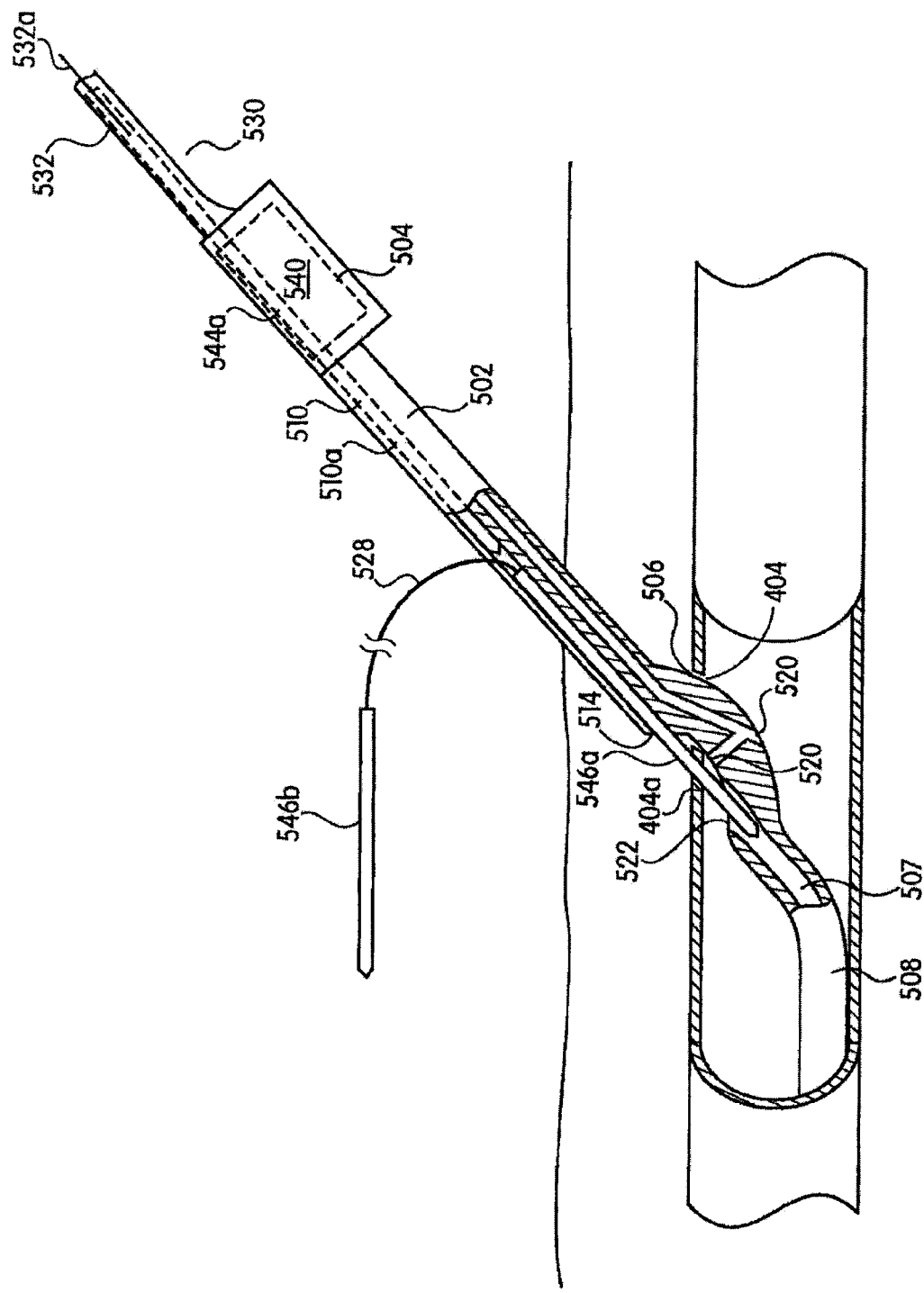
FIG. 10 shows a partial cross-section side view of the device of FIG. 1 in a first position for suturing a blood vessel.

FIG. 10 illustrates the suture device 500 in a first suture position within the puncture 404. In the first suture position, the suture device 500 is suitably positioned to insert a needle through a first side of a puncture 404. Advantageously, the needle cartridge 540 has several needles 546 disposed, e.g., pre-loaded, within its needle slots 544, such as first and second needle slots 544a and 544b. When the suture device 500 is positioned as shown in FIG. 10, the needle cartridge 540 is arranged in a first position within the housing 504. For instance, in this first position, the needle cartridge 540 may be positioned such that the first needle slot 544a is aligned with the central axis 532a of the needle pusher channel 532 and with the central axis 510a of the needle insertion lumen 510 of the proximal part 502. A first needle 546a, having a suture 528 attached at its proximal end, is disposed, e.g., pre-loaded, within the first needle slot 544a. The suture 528 may be formed of either "reabsorbable" or "non-reabsorbable" material, as is well known in the art. In order to actuate the device, the needle pusher 534 is moved distally within the needle pusher channel 532 so as to push the first needle 546a out of the first needle slot 544a and through the needle insertion lumen 510 of the proximal part 502. As shown in FIG. 10, as the pointed distal end of the first needle 546a exits the opening 514 of the needle insertion lumen 510, it penetrates the lining of the blood vessel on a first side 404a of the puncture 404, e.g., the side of the puncture 404 that is disposed within the tissue receiving gap 506a. The first needle 546a is then advanced through the needle receiving opening 522 until the entire first needle 546a is inserted within the distal lumen 507. The needle pusher 530 is then withdrawn back to its original, e.g., proximal-most, position in the needle pusher channel 532.

Figure 11:
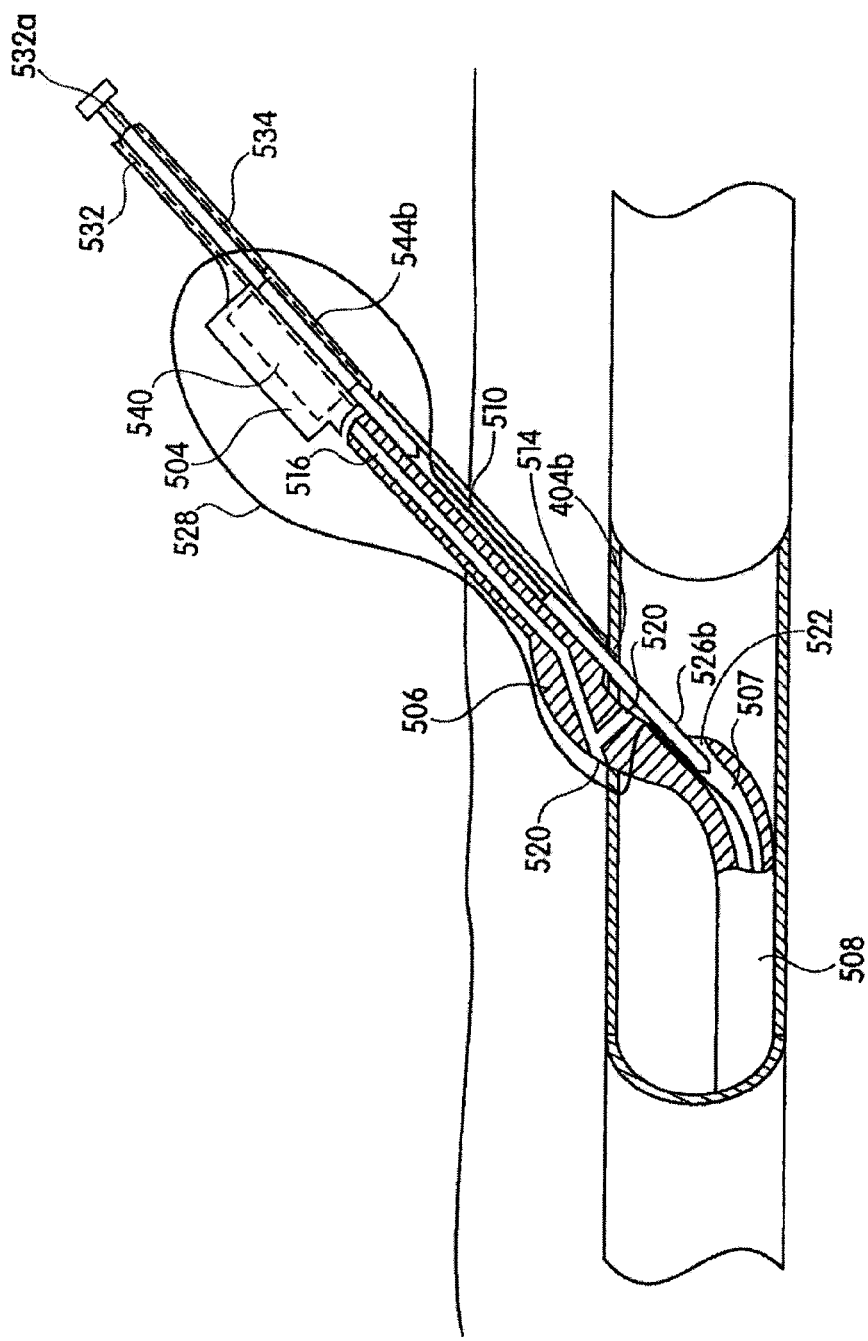
FIG. 11 shows a partial cross-section side view of the device of FIG. 1 in a second position for suturing a blood vessel.

Thereafter, the suture device 500 is rotated into a second suture position. For example, as shown in FIG. 11, the suture device 500 may be rotated 180 degrees so that, in the second suture position, the suture device 500 is positioned to operate on a second side of the puncture 404, e.g., the side opposite from the side of the puncture 404 that was operated on by the suture device 500 in the first suture position. Again, when the suture device 500 is positioned in the second suture position, the position indication lumen 516 and the needle insertion lumen 510 may be observed so as to ensure that a portion of the blood vessel wall is received in the tissue receiving gap 506a between the opening 514 and the needle entry opening 522. Those skilled in the art will understand that any angular separation may be achieved depending, for example, on the number of sutures to be used in sealing the blood vessel.

When the suture device 500 is positioned as shown in FIG. 11, the needle cartridge 540 may be arranged in a second position within the housing 504, such as by an operator moving the needle cartridge 540 within the housing 504 or, for example, by the spring element 542 biasing the needle cartridge 540 towards the second position within the housing 504. In this second position, the needle cartridge 540 may be positioned such that the second needle slot 544b is aligned with the central axis 532a of the needle pusher channel 532 and with the central axis 510a of the needle insertion lumen 510 of the proximal part 502. A second needle 546b, having an opposite end of the suture 528 attached at its proximal end, is disposed, e.g., pre-loaded, within the second needle slot 544b. The needle pusher 534 is then moved distally within the needle pusher channel 532, e.g., from the proximal-most position to the distal-most position so as to move the second needle 546b out of the second needle slot 544b and through the needle insertion lumen 510 of the proximal part 502. As the pointed distal end of the second needle 546b exits the opening 514 of the needle insertion lumen 510, it penetrates the lining of the blood vessel on the opposite side 404b of the puncture 404, e.g., the portion of the blood vessel wall that is disposed within the tissue receiving gap 506a. The second needle 546b is then advanced through the needle receiving opening 522 until the entire second needle 546b is inserted within the distal lumen 507. The needle pusher 530 is then withdrawn back to its original, e.g., proximal-most, position in the needle pusher channel 532.

Figure 12:
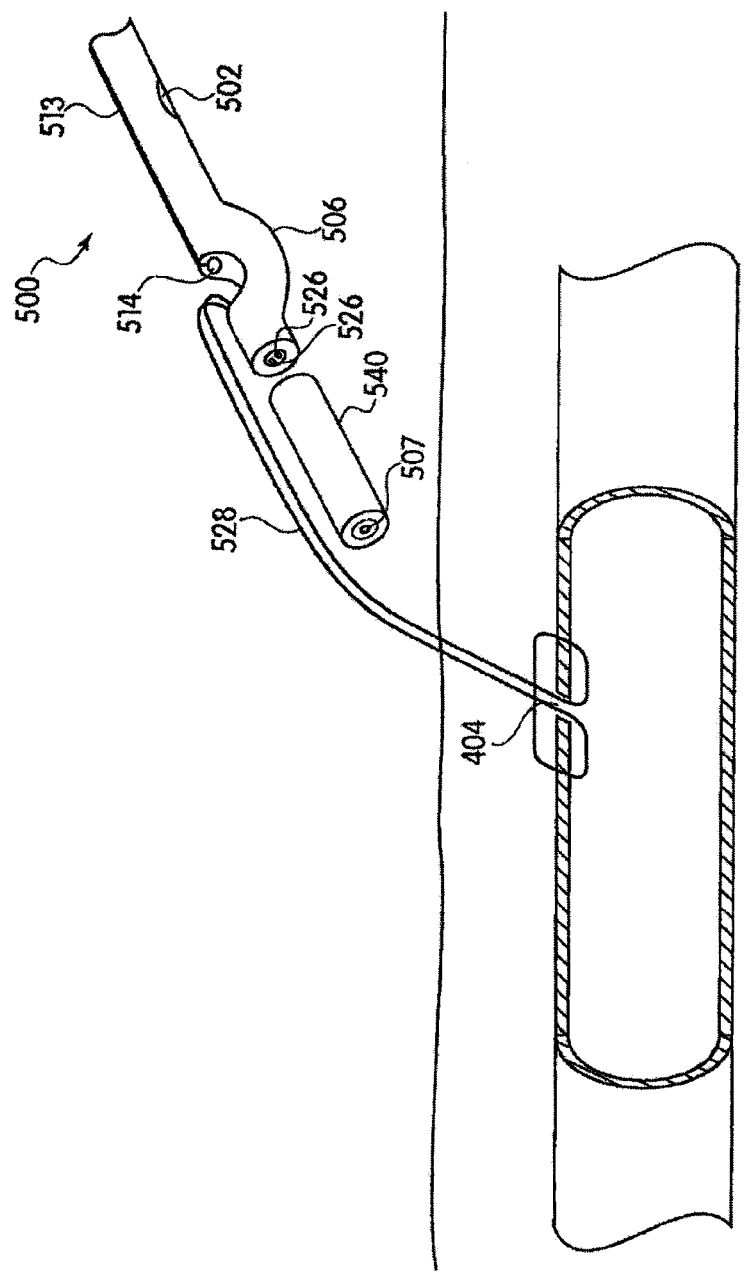
FIG. 12 shows a partial cross-section perspective view of the device of FIG. 1 after removal from the blood vessel.

The suture device 500 is then withdrawn from the body, as illustrated in FIG. 12. As the suture device 500 is withdrawn from the body, the first and second needles 546a and 546b remain within the distal part 508 of the suture device 500. Once the suture device 500 is withdrawn, the suture 528 may then be disconnected, e.g., cut, from the first and second needles 546a and 546b. The two ends of the suture 528 may then be knotted and tightened so as to seal the puncture 404. In one embodiment, the two ends of the suture 528 are different so that a surgeon may differentiate between them during operation. For instance, one or both of the two ends of the suture 528 may be colored or marked so that a surgeon knows how to manipulate the suture ends, e.g., which end of the suture to pull, which end not to pull, etc. As shown in FIG. 12, the configuration of the sutures within the puncture 404 is such that, as the sutures are tightened, the opposite sides of the puncture 404 are drawn together to provide an improved sealing of the puncture 404.

It should be recognized that, while the operation described above illustrates the operation of the suture device 500 shown in FIGS. 1 and 2, a similar operation may be performed when the suture device 1500 shown in FIGS. 13a and 13b is employed. For instance, when the suture device 1500 shown in FIGS. 13a and 13b is employed, the suture device 1500 is placed in a first suture position within a puncture, e.g., positioned to insert a needle through a first side of a puncture. Advantageously, the needle slot 1544 of the needle cartridge 1540 has two or more needles 1546 disposed, e.g., preloaded, within the needle slot 1544. In the first position, the uppermost needle 1546 in the needle slot 1544, e.g., needle 1546a, is aligned with the central axis 1532a of the needle pusher channel 1532 and with the central axis 1510a of the needle insertion lumen 1510 of the proximal part 1502. A first needle 1546a has a suture 1528 attached at its proximal end. The needle pusher 1534 is moved distally within the needle pusher channel 1532 so as to push the first needle 1546a out of the needle slot 1544 and through the needle insertion lumen 1510 of the proximal part 1502. The pointed distal end of the first needle 1546a exits the needle insertion lumen 1510 and penetrates the lining of the blood vessel on a first side of the puncture. The first needle 1546a is then advanced through the needle receiving opening 1522 until the entire first needle 1546a is inserted within the distal lumen 1507. The needle pusher 1530 is then withdrawn back to its original, e.g., proximal-most, position in the needle pusher channel 1532.

Thereafter, the suture device 1500 is rotated into a second suture position so as to operate on a second side of the puncture. Advantageously, in the second position, the next uppermost needle, e.g., needle 1546b, in the needle slot 1544 is aligned with the central axis 1532a of the needle pusher channel 1532 and with the central axis 1510a of the needle insertion lumen 1510 of the proximal part 1502. Specifically, after the needle pusher 1530 has pushed the first needle 1546a out of the needle slot 1544 and after the needle pusher 1530 is withdrawn towards its original, e.g., proximal-most, position in the needle pusher channel 1532, the spring element 1542 biases the needles 1546 within the needle slot 1544 so as to move the second needle 1546b into alignment with the central axis 1532a of the needle pusher channel 1532 and with the central axis 1510a of the needle insertion lumen 1510 of the proximal part 1502. The second needle 1546b has an opposite end of the suture attached at its proximal end. The needle pusher 1534 is then moved distally within the needle pusher channel 1532, e.g., from the proximal-most position to the distal-most position so as to move the second needle 1546b out of the needle slot 1544 and through the needle insertion lumen 1510 of the proximal part 1502. As the pointed distal end of the second needle 1546b exits the needle insertion lumen 1510, it penetrates the lining of the blood vessel on the opposite side of the puncture and is advanced until the entire second needle 1546b is inserted within the distal lumen 1507. The needle pusher 1530 is then withdrawn back to its original, e.g., proximal-most, position in the needle pusher channel 1532.

The suture device 1500 is then withdrawn from the body, such that, as the suture device 500 is withdrawn from the body, the first and second needles 1546a and 1546b remain within the distal part 1508 of the suture device 1500. Once the suture device 1500 is withdrawn, the suture may then be disconnected, e.g., cut, from the first and second needles 1546a and 1546b. The two ends of the suture may then be knotted and tightened so as to seal the puncture.

Figure 14:
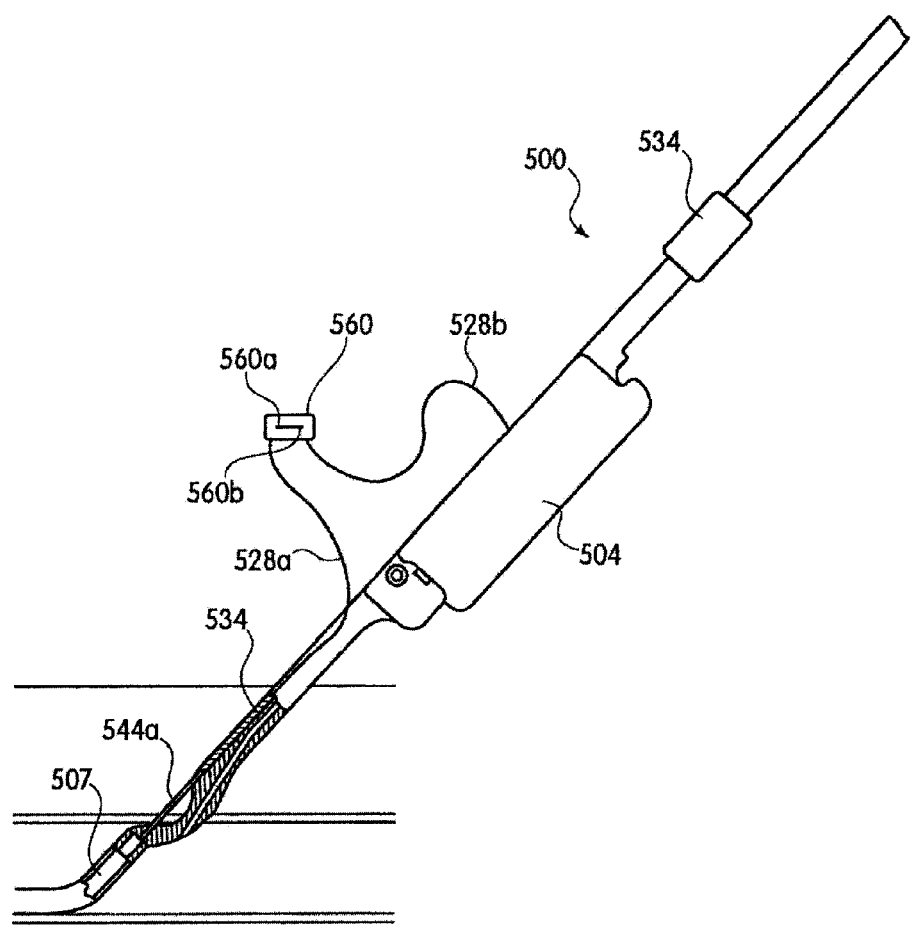
FIGS. 14 to 16 illustrate another process for sealing a puncture, in accordance with another embodiment of the present invention.
Figure 15:
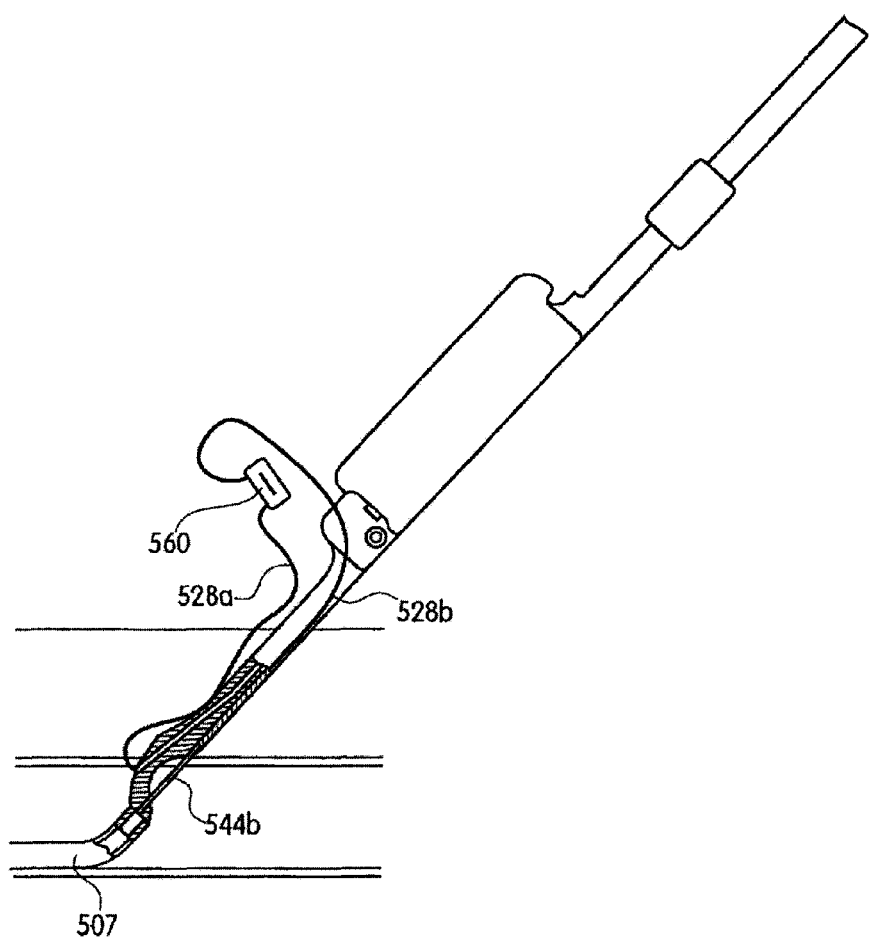
Figure 16:
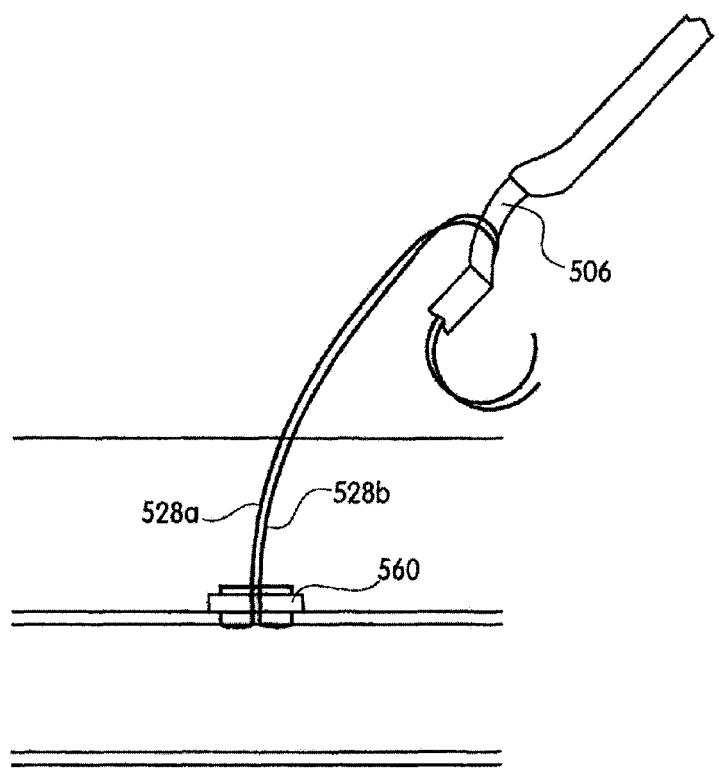

FIGS. 14 to 16 illustrate another process for sealing a puncture in accordance with the present invention, which may be employed with either the suture device 500 shown in FIGS. 1 and 2 or the suture device 1500 shown in FIGS. 13a and 13b. For the purposes of illustration only, the process will be described in connection with the operation of the suture device 500 shown in FIGS. 1 and 2. As shown in FIG. 14, the suture device 500 is placed in a first suture position within a puncture, and the needle pusher 534 is moved distally within the needle pusher channel 532 so as to push the first needle 546a such that the pointed distal end of the first needle 546a penetrates the lining of the blood vessel on a first side of the puncture. The first needle 546a is then advanced until the first needle 546a is inserted within the distal lumen 507, and the needle pusher 530 is withdrawn back to its original, e.g., proximal-most, position in the needle pusher channel 1532. The first needle 546a has a suture 528 attached at its proximal end. In this embodiment, the suture 528 has attached thereto a patch 560 of hemostatic agent. In one embodiment of the present invention, the hemostatic agent includes collagen and may have a sponge or compressed sponge form—however, the present invention contemplates that any type of hemostatic agent in any shape or form may be employed. In the embodiment shown, the hemostatic agent patch 560 has a first hole 560a and a second hole 560b through which the suture 528 is inserted, thereby attaching the hemostatic agent patch 560 to the suture 528. Various other attachment methods may alternatively be employed.

Thereafter, and as shown in FIG. 15, the suture device 500 is rotated into a second suture position. The needle pusher 534 pushes the second needle 546b such that the pointed distal end of the second needle 546b penetrates the lining of the blood vessel on a second side of the puncture. The second needle 546b is then advanced until the second needle 546b is inserted within the distal lumen 507. The second needle 1546b has an opposite end of the suture 528 attached at its proximal. The needle pusher 1530 is then withdrawn back to its original, e.g., proximal-most, position in the needle pusher channel 1532.

The suture device 500 is then withdrawn from the body. As the suture device 500 is withdrawn from the body, the first and second needles 546a and 546b remain within the distal part 508 of the suture device 500. Once the suture device 500 is withdrawn, the suture may then be disconnected, e.g., cut, from the first and second needles 546a and 546b. Either before or after the suture are disconnected from the first and second needles 546a and 546b, the ends of the suture are moved such that the hemostatic agent 560 is positioned against the puncture, thereby helping to seal the puncture. Once the ends of the suture have been moved sufficiently to position the hemostatic plug 560 against the puncture, the suture ends may be knotted and tightened so as to retain the hemostatic agent plug 560 against the blood vessel lining, thereby sealing the puncture.

Figure 18:
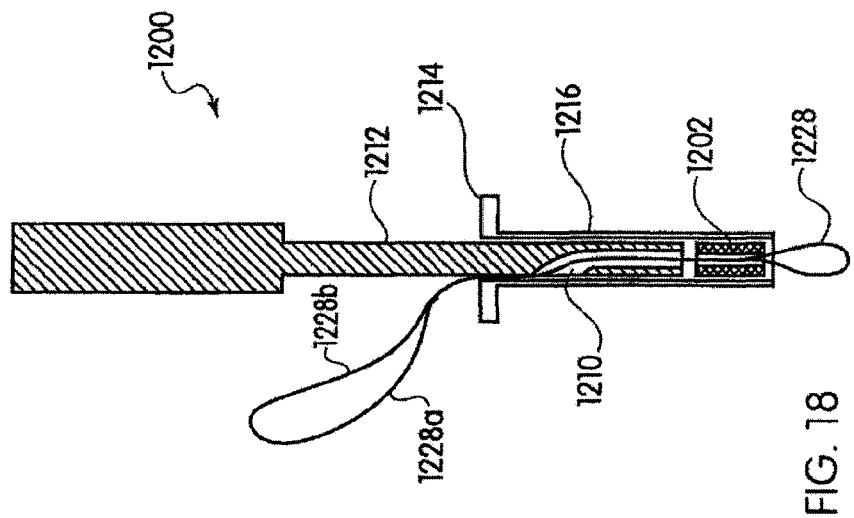
FIGS. 17 and 18 illustrate devices that may be employed to advance a hemostatic agent to a puncture in an anatomical body, in accordance with other embodiments of the present invention.
Figure 17:
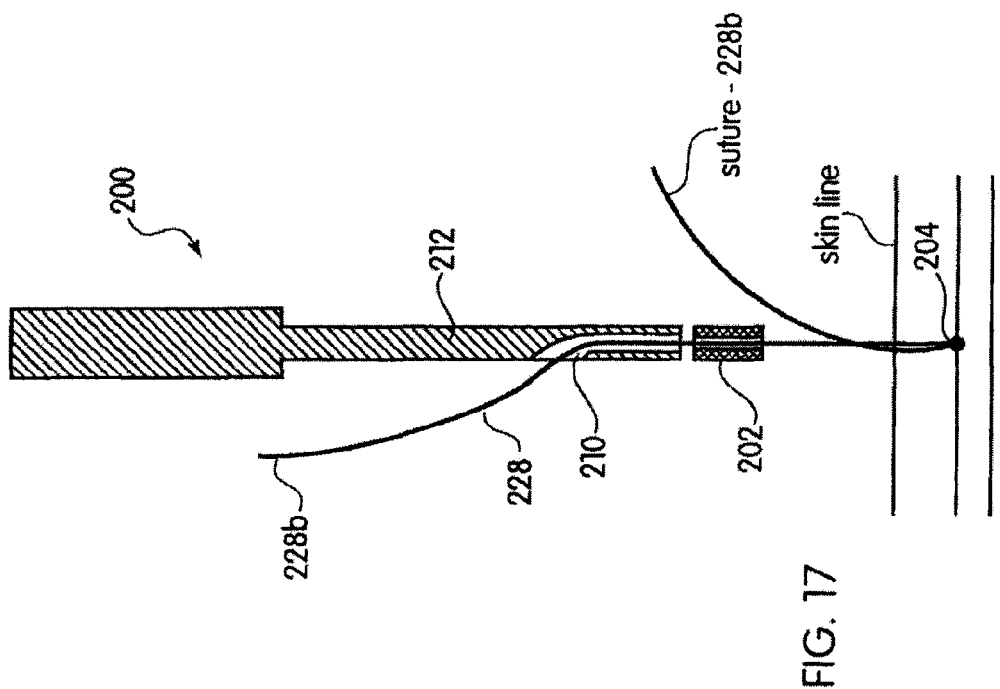

FIGS. 17 and 18 illustrate other devices that may be employed to advance a hemostatic agent to a puncture in an anatomical body. Specifically, FIGS. 17 and 18 illustrate knot pushing devices that are employed to advance a hemostatic plug towards a puncture. Knot pushing devices are typically employed after a knot has been formed in two ends of a suture in order to advance the knot towards and into abutment with the puncture, thereby ensuring that the suture is tight at the puncture location.

FIG. 17 illustrates one embodiment of a knot pushing device 200 in which a knot pushing rod 212 has a curved hole 210 disposed therethrough. Specifically, the curved hole 210 is coaxial with the knot pushing rod 212 at one end of the knot pushing rod 212 but curves so as to exit the side of the knot pushing rod 212. In the embodiment shown in FIG. 17, one end 228a of a suture 228 is threaded through a hole of the hemostatic plug 202 and through the curved hole 210 of the knot pushing rod 212. In this manner, the hemostatic plug 202 is advanced along one end 228a of suture 228 until it reaches the puncture 204.

FIG. 18 illustrates another embodiment of a know pushing device 1200 in which a knot pushing rod 1212 has a curved hole 1210 disposed therethrough. Again, the curved hole 1210 is coaxial with the knot pushing rod 1212 at one end of the knot pushing rod 1212 but curves so as to exit the side of the knot pushing rod 1212. FIG. 18 also illustrates a sheath 1216 having a sheath hub 1214 that is arranged to fit coaxially over the knot pushing rod 1212 and the hemostatic plug 1202. In the embodiment shown in FIG. 18, two ends 1228a and 1228b of a loading snare 1228 are threaded through a hole of the hemostatic plug 1202 and through the curved hole 1210 of the knot pushing rod 1212. The loading snare 1228 is employed to grasp one end of a suture, and is tightened on the end of the suture by the knot pushing rod 1212 being moved distally relative to the sheath 1216. Continued advancement of the knot pushing rod 1212 relative to the sheath 1216 causes the hemostatic plug 1202 to be advanced also. In this manner, the hemostatic plug 1202 is advanced along the loading snare 1228 and along one end of a snared suture until it reaches a puncture.

Those skilled in the art will understand that, for larger punctures, the suture device 500 may be used to insert more than two needles so as to provide as many sutures 528 as are required to seal the puncture. For instance, the suture device 500 may be configured to insert, for example, four needles. In this embodiment, the needle cartridge 540 may have four needle slots 544, each having a needle disposed, e.g., pre-loaded, therein. The suture device 500 may then be used to insert needles at positions 90 degrees relative to each other around the puncture 404, by successively pushing needles through the wall of the blood vessel at various positions around the puncture. In this embodiment, when the suture device 500 has been withdrawn from the body, a first pair of suture ends, which are separated by approximately 180 degrees relative to each other, may be knotted together. Then, a second pair of suture ends, which are separated by approximately 180 degrees relative to each other but separated by approximately 90 degrees relative to the first pair of suture ends, may be knotted together. The two pairs of suture ends may be distinguished by color coding or any similar technique, so as to insure that an operator knots the correct suture ends. Of course, it should be understood that the present invention, according to various embodiments thereof, may employ any number of sutures, used at any positions relative to a puncture or to each other.

There are many other variations of the above described embodiments which will be apparent to those skilled in the art. It is understood that these modifications are within the teaching of the present invention which is to be limited only by the claims appended hereto. In addition, although the operation of the various embodiments has been described in regard to the sealing of an opening in the wall of a blood vessel, those skilled in the art will understand that this invention may also be used to seal openings in various internal organs and structures.

Several embodiments of the present invention are specifically illustrated and/or described herein. However, it will be appreciated that modifications and variations of the present invention are covered by the above teachings without departing from the spirit and intended scope of the present invention.

The invention claimed is:

1. A sealing apparatus for sealing a puncture in an anatomical structure, the sealing apparatus comprising:
   a shaft having a distal portion and a proximal portion;
   a housing located on the proximal portion, the housing having a needle slot, wherein the needle slot having a plurality of needles disposed side-by-side therein;
   the proximal portion of the shaft having a needle insertion and receiving lumen positioned distal of the needle slot, the needle insertion and receiving lumen being arranged and configured to receive an entire one of the plurality of needles;
   the proximal portion of the shaft further having a needle pusher channel, wherein the needle pusher channel having a needle pusher disposed therein, the needle pusher configured to successively advance each of the plurality of needles into the needle insertion and receiving lumen;
   wherein the plurality of needles are movable within the needle slot to be successively positioned in alignment with the needle insertion and receiving lumen and the needle pusher channel; and
   a suture having a first end connected to at least one of the plurality of needles.

2. The sealing apparatus of claim 1, wherein the needle slot further comprises a biasing element configured to move the plurality of needles within the needle slot.

3. The sealing apparatus of claim 1, wherein the needle slot is arranged vertically with respect to a longitudinal axis of the proximal portion of the shaft.

4. The sealing apparatus of claim 1, wherein the suture further comprising a second end connected to a second needle of the plurality of needles.

5. The sealing apparatus of claim 1, wherein the needle pusher successively advances each of the plurality of needles out of a distal end of the needle insertion and receiving lumen.

6. The sealing apparatus of claim 1, wherein the needle insertion and receiving lumen has a length that is greater than a length of any of the plurality of needles.

7. The sealing apparatus of claim 1, further comprising a cartridge positioned in the housing, the cartridge including the needle slot.

8. The device of claim 1, wherein the biasing element is a spring.

9. The device of claim 1, further comprising a hemostatic agent attached to the suture, such that when the sealing apparatus is employed to position the suture in the puncture, the hemostatic agent being configured to be positioned over the puncture.

10. The apparatus of claim 9, wherein the hemostatic agent is a patch.

11. The device of claim 10, wherein the hemostatic agent patch has a pair of holes through which the suture is inserted for attachment.

12. The device of claim 9, wherein the hemostatic agent is collagen.

13. A sealing apparatus for sealing a puncture in an anatomical structure, the sealing apparatus comprising:
a shaft having a distal portion and a proximal portion, the proximal portion comprising:
a needle insertion and receiving lumen;
a needle pusher channel;
a needle pusher disposed in the needle pusher channel;
a device for providing suture needles to the needle and insertion receiving lumen, the device comprising:
a housing positioned proximal of the needle insertion and receiving lumen;
a cartridge mounted in the housing and having a needle slot extending from a distal end of the cartridge to a proximal end of the cartridge and arranged in alignment with the needle insertion and receiving lumen and needle pusher channel, the needle slot having at least first and second needles disposed therein, the cartridge including a biasing member that moves the at least first and second needles within the needle slot to successively positioned each of the at least first and second needles in alignment with the needle insertion and receiving lumen and the needle pusher channel;
wherein the needle insertion and receiving lumen is sized to receive an entire length of at least one of the at least first and second needles; and
a suture having a first end attached to the at least first needle.

14. The sealing apparatus of claim 13, wherein the biasing member is a leaf spring.

15. The sealing apparatus of claim 13, wherein the needle slot is oriented vertically with respect to a longitudinal axis of the proximal portion.

16. The sealing apparatus of claim 13, a wherein the suture further comprising a second end connected to the second needles.

17. The sealing apparatus of claim 13, wherein the needle slot holds at least 5 needles.

18. The sealing apparatus of claim 13, wherein the needle pusher is operable to advance the first or second needle from the cartridge into the needle insertion and receiving lumen.

* * * * *